United States Patent [19]

Dupuis et al.

[11] Patent Number: 5,275,810
[45] Date of Patent: Jan. 4, 1994

[54] COSMETIC COMPOSITION FOR MAINTAINING THE HAIRSTYLE CONTAINING AN OXAZOLINE POLYMER AND A 2-HYDROXY-4-METHOXY-BENZOPHE-NONE-5-SULPHONIC ACID, SALIFIED OR OTHERWISE

[75] Inventors: Christine Dupuis; Jean F. Grollier, both of Paris, France

[73] Assignee: L'Oreal, France

[21] Appl. No.: 768,102

[22] Filed: Sep. 30, 1991

Related U.S. Application Data

[63] Continuation of Ser. No. 313,800, Feb. 22, 1989, abandoned.

[30] Foreign Application Priority Data

Feb. 25, 1988 [LU] Luxembourg ............... 87.142

[51] Int. Cl.$^5$ ............... A61K 7/11; A61K 9/12
[52] U.S. Cl. ............... 424/71; 424/47; 424/DIG. 2; 424/DIG. 1
[58] Field of Search ............... 424/78, 45, 47, 70, 424/71; 514/880, 881; 524/507; 427/160

[56] References Cited

U.S. PATENT DOCUMENTS

| | | | |
|---|---|---|---|
| 3,445,566 | 5/1969 | Skoultchi et al. | 424/71 |
| 3,579,630 | 5/1971 | Herz | 424/47 |
| 4,495,325 | 1/1985 | DeBergalis et al. | 524/507 |
| 4,726,945 | 2/1988 | Patel et al. | 424/70 |
| 4,804,531 | 2/1989 | Grollier | 424/60 |

FOREIGN PATENT DOCUMENTS

| | | |
|---|---|---|
| 0193932 | 9/1986 | European Pat. Off. |
| 1939669 | 2/1971 | Fed. Rep. of Germany |
| 2046818 | 3/1972 | Fed. Rep. of Germany |
| 1553988 | 1/1969 | France |
| 671857 | 5/1952 | United Kingdom |

Primary Examiner—Paul R. Michl
Assistant Examiner—Sally Gardner
Attorney, Agent, or Firm—Marshall, O'Toole, Gerstein, Murray & Borun

[57] ABSTRACT

Cosmetic composition designed to maintain the hair in place, containing, in a cosmetically medium, at least one oxazoline polymer of formula (I):

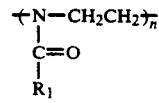

in which $R_1$ denotes a $C_1$–$C_4$ lower alkyl radical and n has a value such that the molecular weight is equal to at least 10,000 and at least one 2-hydroxy-4-methoxybenzophenone-5-sulphonic acid or its cosmetically acceptable salts.

16 Claims, No Drawings

COSMETIC COMPOSITION FOR MAINTAINING THE HAIRSTYLE CONTAINING AN OXAZOLINE POLYMER AND A 2-HYDROXY-4-METHOXY-BENZOPHENONE-5-SULPHONIC ACID, SALIFIED OR OTHERWISE

This application is a continuation of application Ser. No. 07/313,800, filed Feb. 22, 1989 now abandoned.

The present invention relates to a new cosmetic composition designed to be used for maintaining the hair in place, containing an oxazoline polymer and 2-hydroxy-4-methoxybenzophenone-5-sulphonic acid, salified or otherwise.

Polymers derived from oxazoline are known per se, and French Patent 1,553,988 describes, in particular, the application of some of these polymers in hairstyling compositions designed to maintain the hair in place, where the objective is to maintain the set of permanent waving or to fix the style.

These compositions are applied directly on the hair, using a comb or by hand, and are preferably applied by spraying onto the hair, in which case they constitute lacquers.

Oxazoline polymers are entirely suited to this type of application, which requires good solubility in organic solvents such as ethanol and isopropanol and high compatibility with propellants, as well as a ready dispersibility in water in order to be capable of rapid removal from the hair by rinsing or with shampoos.

In addition, these resins do not automatically require the use of additives such as plasticizers, since they themselves form flexible films.

Moreover, the films formed with these polymers are shiny and preserve the waves perfectly well.

The applicant found, however, that, in some cases, oxazoline polymers reacted with the sebum of the hair, naturally secreted by the sebaceous glands, producing an unpleasant sticky effect to the touch and an unattractive appearance of the hair.

The applicant discovered, surprisingly, that the addition of 2-hydroxy-4-methoxybenzophenone-5-sulphonic acid, salified or otherwise to oxazoline polymers enabled this drawback of a sticky effect on the hair to be remedied without, however, modifying the advantageous properties imparted by the said polymers.

The subject of the invention is hence a cosmetic composition designed for maintaining the hair in place, containing at least one oxazoline polymer and at least one 2-hydroxy-4-methoxybenzophenone-5-sulphonic acid, salified or otherwise.

Another subject of the invention consists of a process for the cosmetic treatment of the hair designed to promote maintenance of the latter in place, consisting in applying thereon the combination of at least one oxazoline polymer and at least one 2-hydroxy-4-methoxybenzophenone-5-sulphonic acid, salified or otherwise.

Other subjects of the invention will become apparent on reading the description and the examples which follow.

The cosmetic composition according to the invention is essentially characterized in that it contains, in a cosmetically acceptable medium, at least one oxazoline polymer of formula (I):

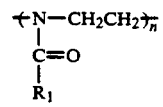

in which $R_1$ is a $C_1$–$C_4$ lower alkyl radical, and preferably an ethyl group, and n has a value such that the molecular weight is equal to at least 10,000, and at least one 2-hydroxy-4-methoxybenzophenone-5-sulphonic acid or its cosmetically acceptable salts.

The cosmetically acceptable salts are chosen from metal salts such as, more especially, alkaline metal and alkaline-earth metal salts, and ammonium and amine salts.

The oxazoline polymers of formula (I) have a molecular weight of more than 10,000, generally of between 20,000 and 1,000,000, and preferably of between 50,000 and 500,000, and are prepared by the polymerization of 2-alkyl-2-oxazoline. The preferred polymers are homopolymers of ethyloxazoline having a molecular weight of between 20,000 and 1,000,000, and more especially those sold by the company DOW CHEMICAL under the name PEOX, having molecular weights of 50,000 to 500,000.

A more especially preferred polymer according to the invention is represented by a homopolymer of ethyloxazoline of molecular weight 50,000.

The 2-hydroxy-4-methoxybenzophenone-5-sulphonic acid used according to the invention is preferably that sold by the company BASF under the name "UVINUL MS 40".

The oxazoline polymer is present in the composition according to the invention in concentrations of between 0.2 and 10% by weight, relative to the total weight of the composition, preferably from 0.5 to 8% and especially between 1.3 and 5% by weight, and the 2-hydroxy-4-methoxybenzoplienone-5-sulphonic acid is used in concentrations preferably of between 0.05 and 2.5% by weight, and more especially between 0.1 and 2% by weight, relative to the total weight of the composition.

The compositions according to the invention can be presented in the form of aqueous, aqueous-alcoholic or alcoholic lotions, optionally thickened, and can preferably be packaged as an aerosol for application in the form of an atomization or spray and to form a lacquer on the hair.

The cosmetically acceptable medium can consist of water and/or a cosmetically acceptable organic solvent such as, more especially, a solvent chosen from monohydric alcohols having from 1 to 8 carbon atoms, for example ethanol, isopropanol, benzyl alcohol and phenylethyl alcohol, and polyhydric alcohols such as alkylene glycols, for example ethylene glycol and propylene glycol, used alone or as mixtures. The solvent is preferably present in proportions of not more than 70% by weight relative to the total weight of the whole composition.

When the compositions are presented in the form of aqueous-alcoholic lotions, the quantity of alcohol present in the composition can be from 5 to 70% by weight, relative to the total weight of the composition.

When the compositions according to the invention are packaged as an aerosol for application in spray form, they are chiefly alcoholic and contain a quantity of alcohol, and in particular ethyl alcohol, in a proportion of 20 to 95%, and more especially 20 to 70%, by weight relative to the total weight of the pressurized composition.

The compositions according to the present invention can contain additives customarily used in cosmetics, which are compatible with the oxazoline polymers of formula (I) and chosen from emollients, lubricants, penetrating agents, stabilizers, perfumes, thickening agents, preservatives and, optionally, plasticizers.

The thickeners used in the compositions according to the invention are preferably chosen from acrylic acid polymers, crosslinked or otherwise, and more especially polyacrylic acids crosslinked with a polyfunctional agent such as the products sold by the company GOODRICH under the name CARBOPOL, cellulose derivatives such as methylcellulose, hydroxyethylcellulose, hydroxypropylmethylcellulose and the sodium salts of carboxymethylcellulose, or high molecular weight ethylene/maleic anhydride copolymers.

These thickeners are present at between 0.05 and 5%, and preferably between 0.1 and 2%, by weight relative to the total weight of the composition.

When the compositions according to the invention are packaged as an aerosol for application in spray form, the propellant agents can be chosen from volatile hydrocarbons such as n-butane, propane and isobutane or mixtures thereof, or a mixture of these hydrocarbons with chlorinated and/or fluorinated hydrocarbons such as the compounds sold by the company DU PONT DE NEMOURS under the name Fréon or Dymel, and more especially fluorochloro hydrocarbons such as monoflurotrichloromethane, difluorodichloromethane, and tetrafluorodichloroethane or mixtures of the latter.

They can also be chosen from the chlorinated and/or fluorinated hydrocarbons described above and mixtures thereof, dimethyl ether,, carbon dioxide and nitrous oxide.

It is preferable, according to the invention, to use a mixture of n-butane, isobutane, propane and monofluorotrichloromethane, and more especially a mixture of n-butane, isobutane and propane.

The propellant phase in these lacquer compositions represents 30 to 80% of the total weight of the pressurized composition.

The compositions according to the invention are used for fixing the hair in place. They can be applied as a treatment product after dyeing or bleaching, after shampooing and after permanent-waving or straightening of the hair.

An especially preferred composition according to the invention consists of a composition for fixing the hair in place in the form of a spray or lacquer.

The process for the cosmetic treatment of the hair designed to promote maintenance of the latter in place, which constitutes another subject of the invention, consists in applying at least one oxazoline polymer (I) and at least one 2-hydroxy-4-methoxybenzophenone-5-sulphonic acid, salified or otherwise, in a cosmetically acceptable medium, on the wet or dried hair, by means of compositions described above, preferably without the application being followed by rinsing.

The examples which follow are designed to illustrate the invention, no limitation of the latter being implied.

EXAMPLE 1

A spray having the following composition is prepared:

| | |
|---|---|
| Polyethyloxazoline of MW 50,000, sold by the company DOW CHEMICAL under the name PEOX | 5.83 g |
| 2-Hydroxy-4-methoxybenzophenone-5-sulphonic acid (BASF UVINUL MS 40) | 0.83 g |
| Perfum qs | |
| Ethyl alcohol, absolute qs | 100.000 g |
| Aerosol packaging: | |
| Composition above | 48.00 g |
| Ternary mixture of n-butane, isobutane > 55% and propane, sold by the company ELF AQUITAINE under the name AEROGAZ 3,2 N | 52.00 g |
| TOTAL | 100.00 g |

EXAMPLE 2

A spray having the following composition is prepared:

| | |
|---|---|
| Polyethyloxazoline of MW 50,000, sold by the company DOW CHEMICAL under the name PEOX | 2.72 g |
| 2-Hydroxy-4-methoxybenzophenone-5-sulphonic acid (BASF UVINUL MS 40) | 0.63 g |
| Perfume qs | |
| Ethyl alcohol, absolute qs | 100.00 g |
| Aerosol packaging: | |
| Composition above | 55.00 g |
| Ternary mixture of n-butane, isobutane >55% and propane, sold by the company ELF AQUITAINE under the name of AEROGAZ 3,2, N | 45.00 g |
| TOTAL | 100.00 g |

EXAMPLE 3

A hairstyling gel having the following composition is prepared:

| | |
|---|---|
| Crosslinked polyacrylic acid, MW 4,000,000, sold by the company GOODRICH under the name CARBOPOL 940 | 1.20 g |
| Polyethyloxazoline of MW 500,000, sold by the company DOW CHEMICAL under the name PEOX | 3.00 g |
| 2-hydroxy-4-methoxybenzophenone-5-sulphonic acid (BASF UNIVUL MS 40) | 0.50 g |
| Diethylenetriainepentaacetic acid pentasodium salt | 0.20 g |
| Ethyl alcohol | 17.20 g |
| Triethanolamine qs pH 7 | |
| Perfume, colouring, qs | |
| Water qsp | 100.00 g |

We claim:

1. Cosmetic composition designed to maintain hair in place, containing, in a cosmetically acceptable medium, 0.2 to 10% by weight of at least one oxazoline polymer of formula (I):

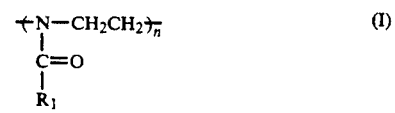

in which $R_1$ is a $C_1$–$C_4$ alkyl radical and n has a value such that the molecular weight is equal to at least 10,000, and 0.05 to 2.5% by weight of at least one 2- hydroxy-4-methoxybenzophenone-5-sulphonic acid or its cosmetically acceptable salts.

2. Cosmetic composition according to claim 1, wherein the oxazoline polymers of formula (I) have a molecular weight of 20,000 to 1,000,000.

3. Composition according to claim 1, wherein the oxazoline polymer of formula (I) is a homopolymer of ethyloxazoline of molecular weight 50,000.

4. Composition according to claim 1, containing at least 0.2 to 10% of oxazoline polymer of formula (I) by weight relative to the total weight of the composition, and at least 0.05 to 2.5% by weight of 2-hydroxy-4-methoxybenzophenone-5-sulphonic acid.

5. Composition according to claim 1, containing, in a cosmetically acceptable medium:
   at least 1.3 to 5% by weight of oxazoline polymer of formula (I); and
   at least 0.1 to 2% by weight of 2-hydroxy-4-methoxybenzophenone 5-sulphonic acid.

6. Composition according to claim 1, which is presented in the form of an aqueous, aqueous-alcoholic or alcoholic lotion.

7. Composition according to claim 1, which is packaged as an aerosol for application in the form of an atomization or spray and to form a lacquer on the hair.

8. Composition according to claim 1, wherein the cosmetically acceptable medium contains water and/or a cosmetically acceptable organic solvent, chosen from monohydric alcohols having from 1 to 8 carbon atoms and polyhydric alcohols, used alone or as mixtures, said solvent being present in proportions of not more than 70% by weight relative to the total weight of the composition.

9. Composition according to claim 1, in the form of an aqueous-alcoholic lotion, wherein the quantity of alcohol present in the composition is between 5 and 70% by weight relative to the total weight of the composition.

10. Composition according to claim 1, packaged as an aerosol in the form of a lacquer which contains from 20 to 95% of alcohol by weight relative to the total weight of the pressurized composition.

11. Composition according to claim 1, which contains additives which are compatible with the oxazoline polymer of formula (I) and chosen from emollients, perfumes, preservatives, thickening agents, lubricants, plasticizers or stabilizers.

12. Composition according to claim 1 which contains from 0.05 to 5% by weight, and preferably from 0.1 to 2% by weight, relative to the total weight of the composition, of a thickening agent chosen from acrylic acid polymers cellulose derivatives or high molecular weight ethylene/maleic anhydride copolymers.

13. Composition according to claim 1, packaged as an aerosol for application in spray form, which contains, in a proportion of 30 to 80% by weight relative to the total weight of the pressurized composition, a propellant agent chosen from n-butane, propane and isobutane or mixtures thereof, or a mixture of these hydrocarbons with chlorinated and/or fluorinated hydrocarbons chosen from monofluorotrichloromethane, difluorodichloromethane, and tetrafluorodichloroethane, mixtures of these fluorinated and/or chlorinated hydrocarbons described above, carbon dioxide, dimethyl ether or nitrous oxide.

14. Composition according to claim 13, which contains a propellant agent chosen from a mixture of n-butane, isobutane, propane and monofluorotrichloromethane, or a mixture of n-butane, propane and isobutane.

15. In a cosmetic composition for maintaining the hairstyle, comprising in a cosmetically acceptable medium 0.2 to 10% by weight of at least one oxazoline polymer of Formula I from claim 1 in which $R_1$ is a $C_1$-$C_4$ alkyl radical and n has a value such that the molecular weight is equal to at least 10,000, the improvement comprising incorporating in said composition 0.05 to 2.5% by weight of at least one member of the group consisting of 2-hydroxy-4-methoxybenzophenone-5-sulphonic acid and its cosmetically acceptable salts.

16. A process for the cosmetic treatment of hair for maintaining the hairstyle, comprising applying to the hair, without rinsing after the application, a composition in accordance with claim 1.

* * * * *